United States Patent [19]

Carlisle

[11] 4,191,184

[45] Mar. 4, 1980

[54] INTRAVENOUS INFUSION REGULATION SYSTEM WITH RECIPROCAL METERING MEANS

[76] Inventor: Jeffrey A. Carlisle, 30 Harris St., Acton, Mass. 01720

[21] Appl. No.: 911,280

[22] Filed: May 31, 1978

Related U.S. Application Data

[63] Continuation-in-part of Ser. No. 757,452, Jan. 6, 1977, abandoned.

[51] Int. Cl.² .............................................. A61M 5/00
[52] U.S. Cl. ........................ 128/214 F; 128/DIG. 12; 128/214 E; 222/249; 222/61
[58] Field of Search ........... 128/214 R, 214 B, 214 E, 128/214 F, 214.2, 227, DIG. 12, DIG. 13; 27/24; 222/61, 249, 250; 73/239–240

[56] References Cited

U.S. PATENT DOCUMENTS

| | | | |
|---|---|---|---|
| 2,625,932 | 1/1953 | Salisbury | 128/214 Z |
| 2,686,952 | 8/1954 | Donahue | 27/24 R |
| 2,772,664 | 12/1956 | Jones et al. | 73/239 |
| 3,208,644 | 9/1965 | Bergson | 222/249 |
| 3,370,759 | 2/1968 | Johansson | 222/249 |
| 3,736,930 | 6/1973 | Georgi | 128/214 E |
| 4,029,094 | 6/1977 | Winicki | 128/214 E |
| 4,121,584 | 10/1978 | Turner et al. | 128/214 E |

*Primary Examiner*—Dalton L. Truluck
*Attorney, Agent, or Firm*—William Nitkin

[57] ABSTRACT

An infusion regulation system for regulating, monitoring, and control of the intravenous infusion of fluids into an animate body. A delivery tube receives and diverges from a fluid supply inlet tube and converges to deliver fluid to an outlet tube to the cannula. A transverse, intermediately positioned volume control tube having a movable control member therein is ported to said divaricated delivery tube. Regulated valve members operate in diagonally paired tandem fashion to control and restrict the flow through the system in an alternating and traverse course. Means for monitoring instantaneous flow through the tubing network allow resistance/pressure changes to be noted and acted upon, either with clinical alarms or through servo mechanisms. Means for selectively increasing the infusate driving pressure allow servo controlled high pressure infusions as well as low pressure, gravity driven infusions.

4 Claims, 4 Drawing Figures

INTRAVENOUS INFUSION REGULATION SYSTEM WITH RECIPROCAL METERING MEANS

BACKGROUND OF THE INVENTION

This application is a continuation in part of my prior application for an Infusion Regulation Apparatus, Ser. No. 757,452 filed Jan. 6, 1977 now abandoned.

The system of this invention relates to the regulation and monitoring of the infusion of fluid into animate bodies. The apparatus of this invention can be utilized with different fluids such as drugs, nutients, blood, etc. The most common practice of infusing fluids into medical patients is accomplished utilizing a fluid container such as a bottle or a bag suspended above the patient with a flexible tube running from the container to the patient through which the fluid flows and enters the patient through a cannula.

It is not only important to regulate the flow of fluids into the patient, but it is also desirable to determine the rate at which the patient is absorbing the fluid since there are different fluid entry resistances for muscular tissue, veins, and arteries. By knowing the resistance pressure at which the patient is taking fluid, one can determine whether the cannula is correctly positioned within the body. Commonly when a direct tube from a suspended fluid container is used, it is very difficult for a nurse or other attendant to accurately judge the rate of flow of fluid into the patient and much time can elapse before it is realized that the cannula may be improperly positioned in the body causing fluid to enter the wrong tissue or to otherwise be obstructed.

The prior art may be broken generally into two major groups: those devices which utilize gravity as the fluid driving power; and those which utilize some positive pressure driving force usually in the form of a motor driven device.

Devices which use the gravitational, hydrostatic pressure of the fluid source to drive the fluid into the patient suffer from several important clinical defects. Such devices generally involve a modulated constriction of a conduit running from a fluid source to the patient infusion connection. The modulation is based on on the frequency of drops leaving the fluid source. It is well documented that the size of these drops is neither accurately known nor reproducible. Small, normal changes in infusion site pressure, due to patient motion, coughing, or fluid source motion can all have deleterious effects on the amount of medication received by the patient. These inaccuracies are most prevalent, and most harmful, at slow flow rates (1–20 ml/hr). Gravity drip controllers do have the distinct advantage of operating at low pressures and this enables the flow rate to react in a sensitive manner to resistance pressure changes.

To overcome the inaccuracies inherent in a gravity drip controller, many varieties of positive pressure pumping devices have been designed. By utilizing various motors, transmissions, and fluid interfaces, these positive pressure devices can acheive a wide range of flow rates with much greater accuracy than drip rate controllers. Practically speaking, the devices assume many different shapes—peristaltic pumps, syringe pumps, or cassette pumps. While these devices allow accurate infusions they are insensitive to slight pressure changes at the infusion site. The motors used must be powerful enough to cause steady, accurate movement of the driving mechanism. If the infusion pressure were to change, the pump could not sense this change and the flow of fluid would continue without regard to this clinically significant pressure change. During long term intravenous infusions, it is important to monitor the status of the infusion site. The cannula or needle entering the vein should be completely within the vessel, non-leaking, and free from obstruction. Determination of these characteristics requires a more sensitive mechanism than possible with a positive pressure device. Positive pressure devices have the desirable ability to infuse into higher pressures, such as into an artery.

Therefore it is an object of this invention to provide a device which can quickly and accurately regulate the flow of fluid, to determine the fluid entry resistance pressure within the tissue, and to use this pressure information to optimize the clinical efficacy of the infusion system.

The system of this invention synergistically utilizes a combination of previously disclosed techniques to acheive clinical benefits enjoyed by no individual device in the prior art. The ability to dispense accurate, discrete, volumetric amounts of infusate over a wide range of delivery pressures; the ability to monitor the flow/pressure/resistance characteristics of an indwelling intravenous line; the ability to servo control the degree of pressure assist during an infusion; and the ability to be integrated into a portable, computer compatible, clinically oriented device are, in total, unique to the invention.

SUMMARY

The present invention consists of an improved method and system for controlling and monitoring intravenous infusions. The invention includes a set of valves with controls to allow fluid flow to reciprocate through a chamber of known volume, such that the net flow is discrete, discontinuous, and unidirectional going from a fluid supply into an animate body. The infusion rate is dependent upon the logically controlled valving system and the apparatus can operate equally well over a wide range of fluid supply/patient pressure gradients. When fluid travels through the volume control chamber, its flow is monitored by measuring the transit time of a freely moving member going from one end of said control chamber to the other. This monitoring is done externally by detecting the position of this control member through the tubing network. The external position detectors do not affect the motion of the control member, allowing the size and mass of the member to be optimally selected. The transit time measurements are indicative of clinically significant pressures within the patient. Means are also provided to create adjustable, external infusion pressures without affecting the overall infusion rate. Detection means for providing clinically relevant safety checks of the system are further provided.

The present invention discloses an infusion regulation system which can monitor and control the infusion flow rate of fluids within a wide range including from 0.5 ml/hr to 300 ml/hr. The apparatus contains a fluid volume control and delivery unit, an external pump unit to generate driving pressures in excess of those available from gravity, and associated electronic controls to select the fluid flow rate to be infused and to determine the volume to be infused in total. Furthermore, the external pressure generated by the external pump unit may be proportionally applied to the infusate source via a mechanical linkage adjustment. This adjustment can be made manually or under automatic servo control. The apparatus further includes safety detection and metering means with appropriate alarm systems upon detection of malfunctions should the fluid flow decrease substantially or the fluid container run dry.

The fluid volume control unit is affixed to an inlet tube extending from a fluid supply container and is comprised of a delivery tube or tubes and a volume control tube. The delivery tube receives the inlet tube, diverges, and then converges to join and receive the outlet tube which leads to the cannula for fluid infusion into the patient. Of course the delivery tube could consist of two or more independent tubes connected, but preferably is an integrated ported structure. Intermediately located between and ported to the divaricated delivery tube portions is a volume control tube. This transverse column chamber is of a predetermined volume and has within it a control member which moves freely from one end of the volume control chamber, which is preferably in a horizontal position, to the other end by the force of the fluid entering the control chamber behind the movable member. It is imperative that the tubing be sterilizable and biologically unreactive. A series of pinch valves are located on the divaricated delivery tube on both sides of each port connection with the volume control tube thus interposing the ported openings into the delivery tube therebetween. These pinch valves operate in an alternating sequence to cause an alternating transverse vourse of a predetermined amount of fluid dlow through the control unit by means of diagonally opposing valves which open and close in tandem pairs. This action is common to other types of metering apparatus and is best illustrated in connection with the drawings.

All fluid passing through the control unit is caused to pass through the volume control chamber in alternating directions. This movement sequence continues with the control member moving back and forth within the horizontal volume chamber. The volume entering the outlet tube is known by determining the number of times the control member moves back and forth within the horizontal volume chamber. The size and construction of the control mechanism must be optimized to allow acceptable clinical dynamic range and accuracy, yet remain within production capabilities. The use of small control tube volumes is fundamentally important to acheive necessarily slow intravenous flow rates. Smaller volumes allow each infusion cycle to represent a smaller bolus of fluid entering the patient, a clinically desirable effect. Conversely, the use of large control tube volumes is important to acheive accurate dimensions and tolerances in manufacturing. Larger volumes allow a percentage reduction in volume error per cycle. Furthermore, the production materials must be chosen such that the specific gravity of the control member is nearly that of the infusate to eliminate internal leakage due to differences in control member/infusate inertial mass. This potential internal leakage is aggrevated by the low infusion pressures used in intravenous therapy. Metering mechanisms in the prior art, although similar in principle, are not adequately designed for use as general purpose intravenous infusion devices in terms of their physical size, composition, or construction.

The control member can be a cylindrical ball moving within a horizontal volume chamber which can be of plastic or equivalent construction. To determine the frequncy and velocity of movement of the control member, detectors are located at each end of the horizontal volume chamber. These detectors can be optical detectors or any equivalent detectors capable of determining the presence of the control member at the end positions of the horizontal volume chamber. The sequence of the operation of the pinch valves and the amount of fluid allowed to be infused thereby is regulated by control circuitry where one may enter the desired flow rate in ml/hr and irregularities of the flow rate are detected by the detectors and monitored by the control circuitry.

If there is increased pressure resistance within a patient whereby fluid is not being accepted at the ordinary rate, the control member's progress through the chamber will be delayed, the quantum of delay being calculated and noted by control circuitry. The amount of time which the control member takes to move from one end of the volume control chamber to the other is a "time elapsed" measurement, which may be analyzed in a variety of ways. The measurement of "time elapsed" will indicate to the patient's attendant whether the patient is accepting the infusate at a normal rate. Inconsistent readings could indicate that the cannula should be checked for malpositioning, whether the rate is too slow or too fast, or checked for crimping or occlusion in the delivery tube system.

A graphic recorder or other long term meter recording device may be connected to this circuitry to show changes in the rate of acceptance of fluid and fluctuations which could indicate important changes in the condition of the patient. Similarly, the "elapsed time" output could be made in a digital format, facilitating communication to other intelligent devices such as computer systems. Knowledge of "elapsed time" changes can be significant in determining the proper course of treatment. One of the important aspects of this system is the determination of the pressure gradient between the volume of fluid desired to be infused and the infusion site.

A further element within the device of this invention is a pump assist mechanism located along the inlet tube. This external pump preferably consists of a peristaltic type arrangement of cams located on a shaft which is placed in engagement with a pusher block. The inlet tube is interposed between the camshaft and pusher block forcing the fluid in the inlet tube to be pumped with peristaltic action in a single direction towards the outlet tube and to the patient. The degree of occlusion of the inlet tube by the pusher block determines the maximum pressure that can be generated by the pumping mechanism. This degree of occlusion may be servo controlled by the control circuitry as a function of the "elapsed time" measurement. In this way, the source pressure could be controlled to yield a nearly constant "elapsed time" measurement. The servo controlled position of the pusher block assembly can be made to minimize the pressure assist necessary for a given infusion rate which effectively maximizes the system's sensitivity to clinically significant resistance pressure changes. The external pump can have various circuit control means for activation and alert signals during its pumping cycle so that an individual can quickly determine the status of the pump operation.

Futher, as a safety mechanism, if the fluid runs out in the container, the control member, even though the pinch valves may open, will not be moved and the detector circuitry sensing the delay in movement will set off appropriate audio-visual alarms. The control circuit, consisting of a microprocessor and associated interface circuitry, allows digital input of flow and rate information and allows a single alphanumeric display to indicate various conditions and alarms. This display may consist of an array of light emitting diodes which will indicate the system's status of flow rate, volume limits, volume infused, low battery charge, purge warnings, keyboard entry errors, slow flow conditions, and volume limit alarms.

Further features and advantages of the present invention will become apparent from the following drawings and Description of the Preferred Embodiment.

DESCRIPTION OF THE PREFERRED EMBODIMENT

Figure 1:
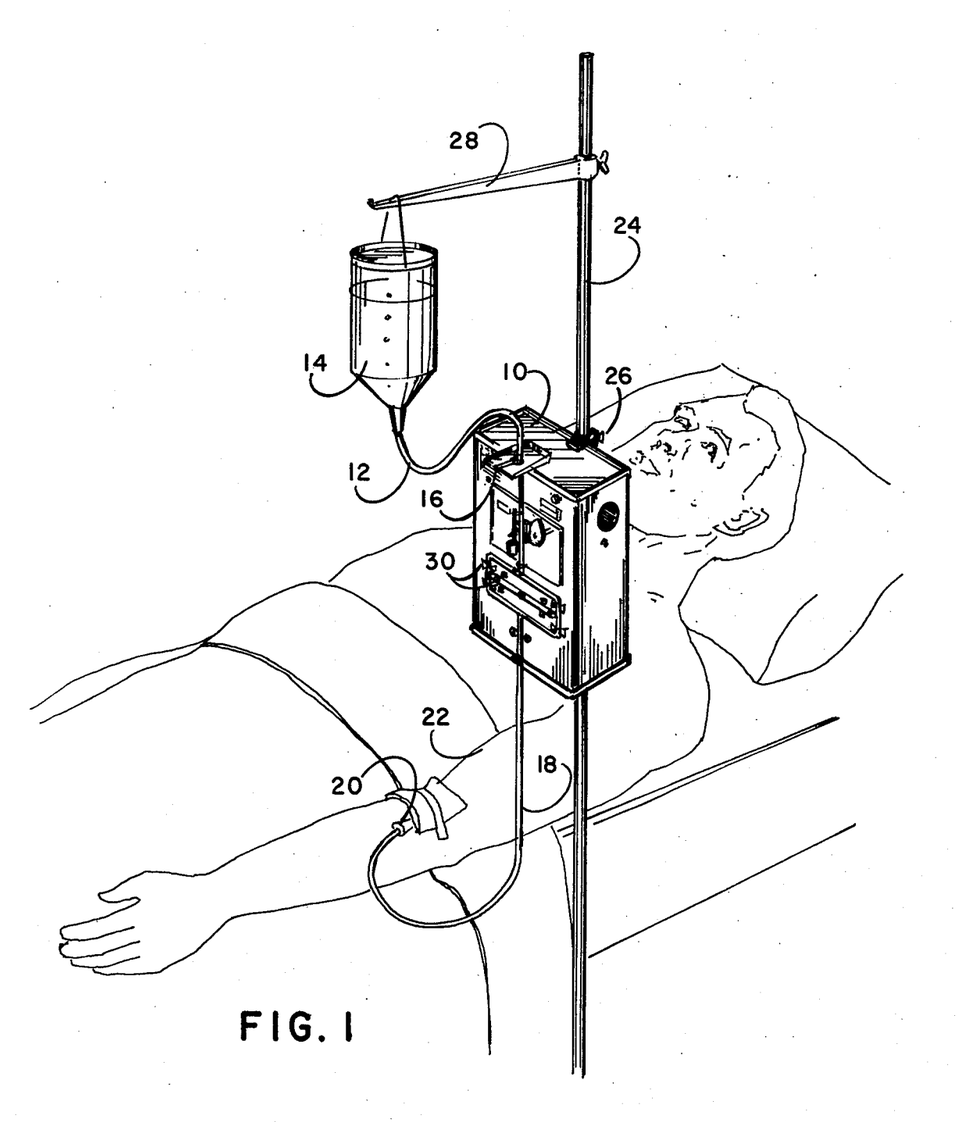
FIG. 1 illustrates the infusion regulation system of the present invention when in use with a medical patient.

Referring now to the drawings and in particular to FIG. 1, the infusion regulation system of the present invention is generally designated by reference numeral 10 with the volume control apparatus being generally designated 30. Inlet tube 12, feeding control unit apparatus 30, connects fluid chamber source 14 and may pass through and/or be affixed to a drip splash shield 16. Shield 16 will catch and prevent fluid which may leak from source 14 onto infusion system 10. Outlet tube 18, connected to control unit 30, is illustrated connected to and feeding cannula 20 which is inserted into animate body 22.

As is normal in the art, infusion device 10 and fluid source 14 are elevated above the patient and mounted upon a stand 24. Appropriate bracket means 26 and 28 may be used to affix these components.

Figure 2:
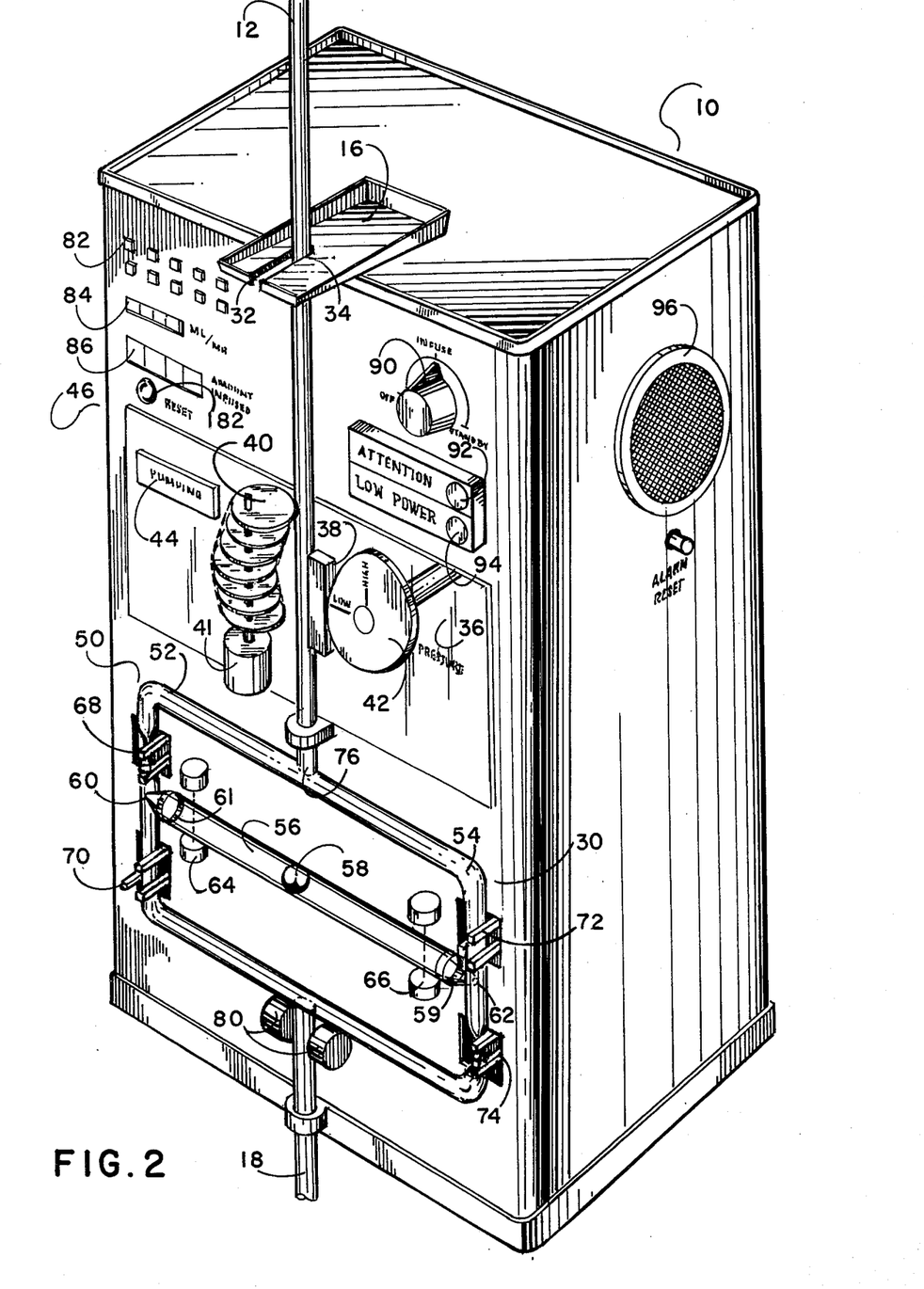
FIG. 2 illustrates a perspective view of the system of FIG. 1.

Turning now to FIG. 2, a perspective view of the infusion system 10 of the present invention is illustrated showing inlet tube 12 passing through splash shield 16 and communicating with control apparatus 30. Inlet tube 12 may be held against the top of infusion pump 10 by splash shield 16 having a retaining clip or similar means, or may pass through a slotted narrow opening 32 to aperture 34 which corresponds to the diameter of inlet tube 12. It is simply desired that the tube be retained in a relatively stationary position and be adapted for easy removal therefrom after use.

Inlet tube 12 may pass through a pumping mechanism which may be of any type which affects the movement of fluids within the tube, but preferably the pump is of the peristaltic type as illustrated. Peristaltic pump unit, generally designated 36, comprises a pump mechanism having a pusher block 38, which is horizontally located by the position of rotatable, eccentric wheel 42. Wheel 42 also acts as an electrical switch, connecting the pump motor 41 to the motor's logical control circuitry. When the pump motor 41 is activated by switch 42 and the device's control circuitry, the rotatable fingers 40, move about a vertical axis. Pusher block 38 provides adjustable occlusion of tube 12, depending on the horizontal position of block 38. The rotation of eccentric wheel 42, forcing the pusher block to move the inlet tube against the peristaltic pump mechanism creates a greater pressure and greater flow, in a manner well known in the art. The maximum delivered pressure is determined by the degree of occlusion of tube 12. The position of wheel 42 dictates the degree of occlusion and may be under servo position control. Wheel 42 may be connected to an internal position sensitive mechanism, such as a stepper motor, which could be advanced or retarded to acheive an optimal delivered pressure. The microprocessor controlled servo means facilitates the use of feedback algorithms for optimizing the clinical operation of the system. A visual indicator 44 on the fromt panel 46, which may be a light emitting diode or similar device, may indicate when the pump is in its operational mode.

The fluid passing down the inlet tube 12 enters the regulatory volume control unit 30. Regulatory volume control unit is preferably comprised of one appropriately ported tubing member 50 for delivery of the fluid to outlet tube 18 but delivery tube 50 may be comprised of two or more attatched units. Regulatory delivery tube 50 diverges and thus separates the flow of fluid and two distinct divaricated portions 52 and 54 are defined thereby to accept the fluid flow. Regulatory delivery tube portions 52 and 54 then converge to feed the outlet tube 18.

Intermediately positioned between divaricated delivery tube 50, i.e. portions 52 and 54, is volume control tube 56 which is, at its ends, affixed thereto and ported therewith. Within volume control tube 56 is a control member 58 which is movably positioned therein.

It is desirable that control member 58 nearly make contact with the circumference of the volume chamber 56 and that it be movable by the entry and exit of fluids into either port 60 or 62. It is desirable that at ends of the volume chamber where they enter the ports that they be constructed in such a manner that when control member 58 is located at an end, it forms a fluid-sealing relationship against fluid wishing to escape from the volume chamber into delivery tube 50. As illustrated, concentric, thin-walled cylindrical inserts 59 and 61 have been devised. In actual practice, this use of inserts would probably be replaced by a specially designed "T" fitting located at ports 60 and 62. During normal operation the control member 58 will not necessarily seat itself against either insert 59 or 61. The presence of inserts 59 and 61 prevents control member 58 from leaving control tube 56.

Detection devices collectively numbered 64 and 66 are located outside of the volume control tube 56 in close association to the ends of the control tube at the juncture with the delivery tube portions 52 and 54. These detection devices may be optical detectors which would be sensitive to the position of the control member when it is moved into their range. It could also be magnetic if used with a metallic control member. These detectors sense the presence of the control member when it is at its farthest end movement within the volume chamber. These detectors send signals to the logical control circuitry to regulate the behavior of the infusion system. Available designs allow these detectors to behave precisely and reproducibly.

The means of regulating the direction of flow through control unit 30 are preferably a system of pinch valves 68, 70,72,74 capable of restricting the flow through delivery tube 50. Two pinch valves 68 and 70 are positioned to interpose volume control port 60 therebetween and two pinch valves 72 and 74 are positioned to interpose volume port 62 therebetween. In operation, diagonally opposed pinch valves will be operated by control means in their opening and closing functions in tandem paired fashion; thus valves 68 and 74 will be open and allow fluid flow when valves 70 and 72 are closed. This action causes fluid flow from inlet tube 12 to outlet tube 18 to course in a traverse manner through a delivery tube portion to the volume control member tube and then to the complementary delivery tube portion on to outlet tube 18.

In practice, as fluid progresses down inlet tube 12, it may receive further pressure from pumping mechanism 36 prior to its entry through port 76 into delivery tube 50. If the cycles of the pinch valves are such that the diagonally opposing paired valves 68 and 74 are closed, the fluid stops at these points. The fluid has thus progressed through the open pinch valve 72 and will progress through port 62 into volume control chamber 56 forcing control member 58, including the fluid before that member to pass to, and the fluid through, port 60. The fluid passes through open valve 70 of delivery tube 50 to outlet tube 18. When control member 58 reaches the end of the control tube 56 located near port 60, it is detected by detector 64. Detector 64 signals the control circuitry to move the pinch valves to the all closed position. In this all closed position, flow ceases to outlet tube 18. As a function of the desired flow rate, the control circuitry activates the next infusion cycle. The next infusion cycle calls for the opposite pair of valves to open than were open on the previous cycle. In this case, valves 68 and 74 will open, valves 70 and 72 remaining closed. Fluid then flows through valve 68 to move control member 58 and the fluid before it to port 62. The fluid passes open valve 74 to outlet tube 18. Detector 66 is responsive to the control member 58 within control tube 56 nearest port 62. The detection causes the four valves to go to the all closed position, awaiting the activation of the next infusion cycle by the control circuitry. It should be noted that the pinch valves prevent any backup of fluid into the inlet tube and they prevent gaps from forming during the cycle which could introduce air into the system.

As this cyclical process repeats, the movement of the control member back and forth in the volume control chamber, and the frequency thereof, is recorded by its detection at the ports and computed within control circuitry to yield the amount in milliliters of fluid infused into the patient through outlet tube 18 and cannula 20.

The fluid control unit along with the inlet and outlet tubes can be constructed of a disposable one-piece sterile plastic or equivalent tubing network and the control member can also be constructed of plastic or other approved material. The volume chamber can be constructed of molded or machined plastic or any equivalent material in which the control member can be engaged in a close fitting relationship yet have freedom of movement. The control member should be constructed of materials with a specific gravity similar to that of common intravenous infusates. The control member and control tube should have nearly equal coefficients of thermal expansion to maintain a reasonably constant amount of slip between the two components.

Also seen on the face of the infusion regulator system is bubble detector 80 which is most usually an electrical component which passes light from one member of the detector to the other member through outlet tube 18. If a bubble passes through the tube, it affects the way light is absorbed and this will vary the level of the voltage in the detector. An alarm will be activated so that one may check to prevent bubbles from progressing down the tube toward the patient. A porous filter may also be used in line between the bubble detector and the patient. This is a very coarse filter designed to prevent large elements, such as glass or coagulated compounds, from being passed into the patient's body where they could inflict serious damage.

On front panel 46 of the unit is seen keyboard 82 where the individual attending the patient will enter the desired ml/hr flow rate for which the regulation system will operate. This flow rate will appear in the ml/hr display 84 which can be composed of LED components and will, through the control circuitry discussed below, activate the operation of the pinch valves on the volume control tubes. Indicator 86, through the control circuitry, will display the volume of fluid actually infused into the patient in milliliters. This volume is based on the number of completed transverse movements completed by control member 58.

On the upper right hand face of the machine is an OFF/INFUSE and STANDBY switch 90. In the off state there is no power going to the regulation device. Everything is shut down and all valves 68,70,72,74 will be in a closed position. In the infuse mode, the infusion regulation system will be activated and the control member and pinch valves will be operating as a function of the flow rate set on keyboard 82 and displayed on ml/hr display 84. The standby mode will allow the attendant to enter data onto keyboard 82 and will allow all of the valves to be opened manually so that fluid can be passed through the inlet tube, the delivery tube, the volume chamber and the outlet tube, all of which may be full of air. This procedure allows the tubing to be completely fluid filled so that when the system is activated, an accurate count may be kept of fluid infused after purging the lines.

Further on the face of the unit is an attention light 92 which will flash if signals from the control circuitry discussed below activate it under a variety of circumstances. Below the attention light is a low power light 94 which is activated if the battery supply voltage drops below a predetermined value. Seen on the side of the unit is audio alarm 96 which would be activated under a variety of circumstances discussed below regarding the control circuitry.

Figure 3:
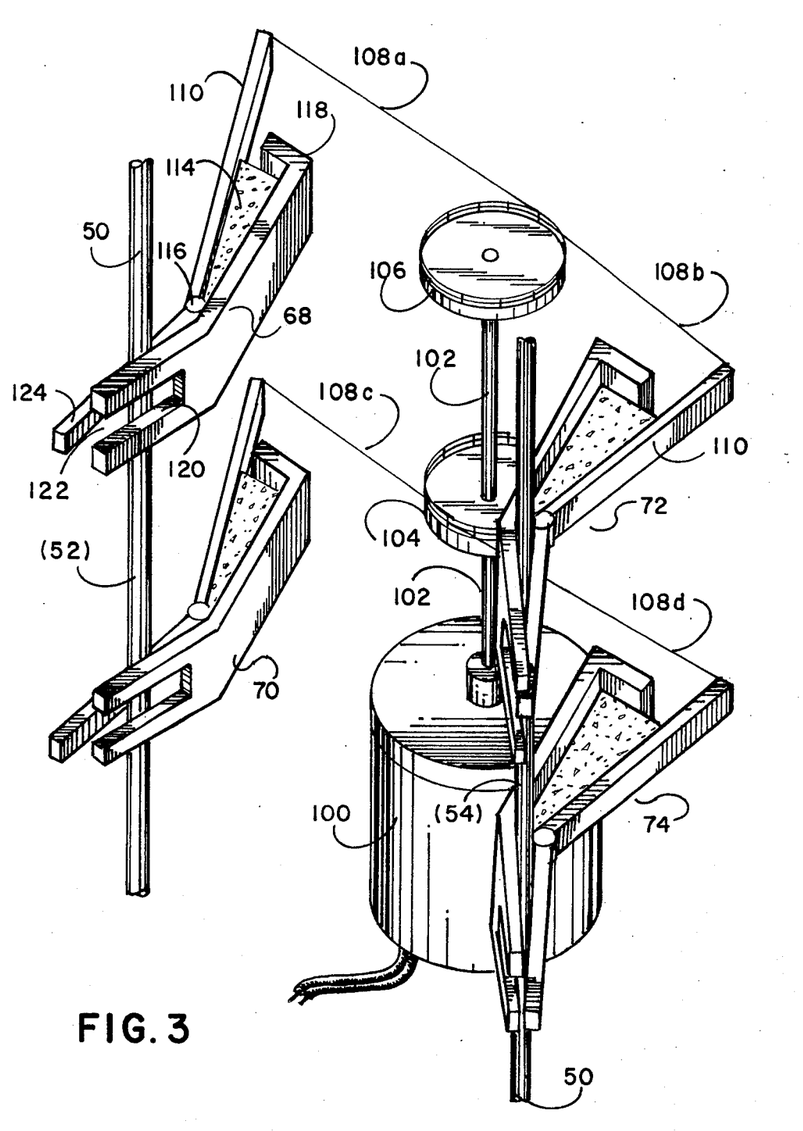
FIG. 3 illustrates an embodiment of the infusion flow direction regulation means of the system of FIG. 2 comprising pinch valves and associated operational mechanisms.

FIG. 3 illustrates the mechanism of the pinch valves. Seen in this view are the pinch valves with delivery tube 50 (52) (54) in outline form without the casing of the unit to obstruct the view of the operative mechanism. In this embodiment pinch valve levers are controlled within the unit by actuating cables wound around a pulley and affixed to a stepper motor which can operate in a +or−20° rotation. Seen in this view is stepper motor 100 and related shaft 102 having thereon two pulleys, 104 and 106. It may be noted that one pulley will suffice to accomplish the task of moving the cables, but for the sake of explanation two pulleys are shown.

The actuator cables 108a,b,c, and d extend from each pulley to each pinch valve lever 110. Actuator cable 108a extending to the pinch valve 68 is seen coming around the righthand side of pulley 106 and there affixed. Actuator cable 108b coming from the pinch valve 72 goes around the lefthand side of pulley 106 and is there affixed. In practice when the stepper motor rotates 20° in one direction (right), one of the actuator cables (108b) is unaffected and left limp, while the other (108a) has tension applied thereto. Pinch valve 72 remains closed. This inward pressure, as illustrated on pinch valve 68, compresses rubber member 114 and causes the obtusely angled pinch valve lever member 110 to pivot on hinged axis 116 and move toward block member 118 releasing pressure against the delivery tube 50. This allows fluid to flow through volume control tube at that point. When the stepper motor reverses the direction of the pulley, this actuating cable (108a) is released and the resilient member 114 forces lever member 110 back into its position where it pinches delivery tube 50 against stationary laterally extending U-shaped member 120 which has an opening 122. End 124 of obtusely angled lever member 110 enters opening 122 thereby creating a more secure pinch against the delivery tube. Pinch valves 70 and 74 are also illustrated below pinch valves 68 and 72 and their actuating cables, 108c and 108d, are wrapped around pulley 104 in opposing directions to the actuating cables of pinch valves 68 and 72 to acheive the aforesaid diagonally paired tandem opening and closing of the pinch valves. It should be noted that the individual operation and structure of pinch valves 70 and 74 is identical to that recited above in relation to pinch valves 68 and 72. Further it should be noted that the cables are of such a length that all pinch valves will be closed when the stepper motor is in a neutral position. It will also be noted that this or a similar mechanical linkage prevents any direct connection of the fluid source to the patient by directing all flow to pass through control tube 56.

Resilient member 114 may be composed of soft rubber or equivalent materials. The stationary plate and lever members are seen to extend beyond the control tube somewhat more than what may be necessary to merely pinch the tube. This is so they can be operated manually by fingers if there is any malfunction of the machine in order to correct or quickly make changes in the direction of flow. The description of the preferred valving embodiment is not intended to suggest actual materials and/or construction techniques, but is to illustrate one viable approach to the mechanical interface necessary for a simple and safe infusion regulation system.

Figure 4:
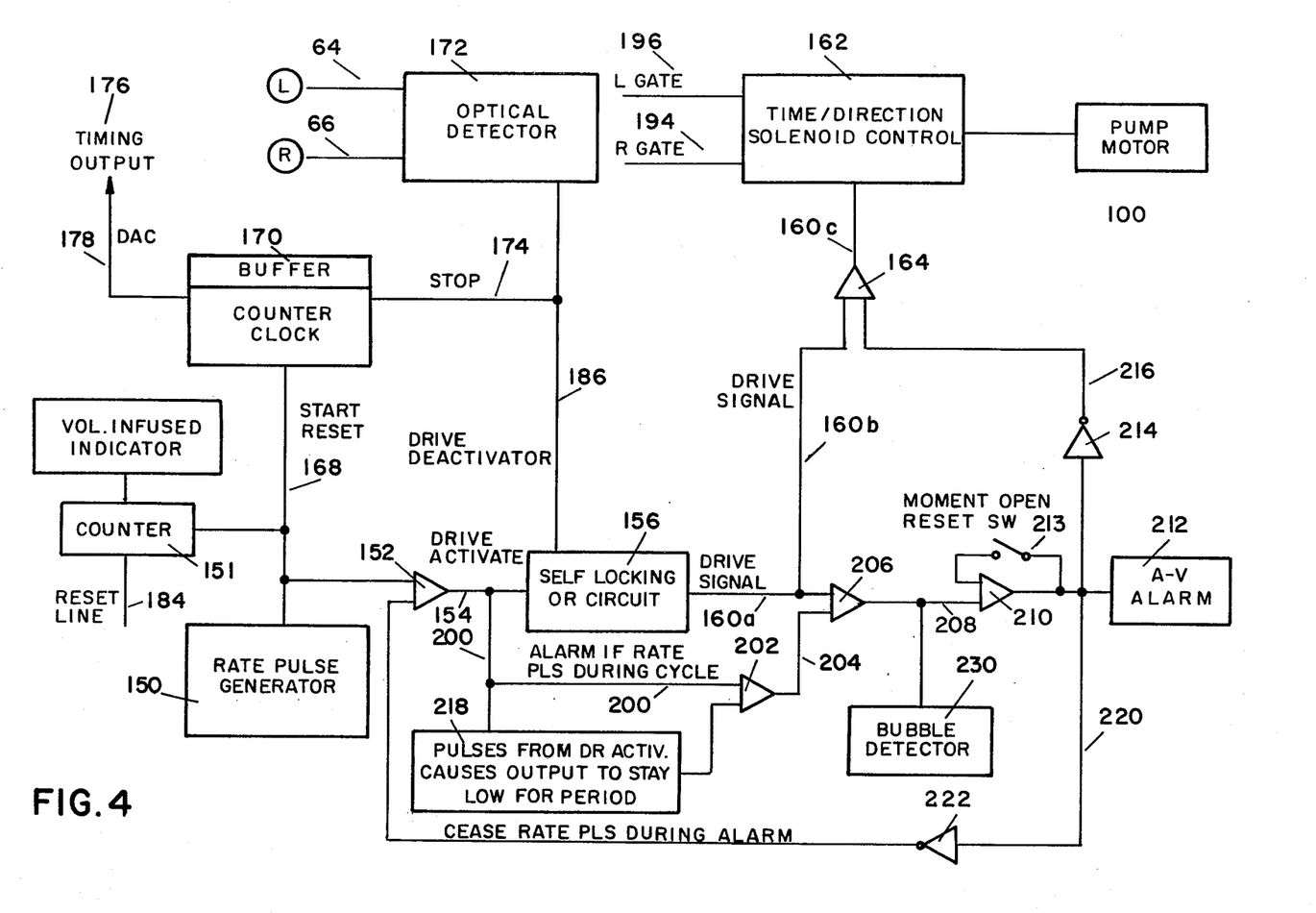
FIG. 4 represents an illustrative block diagram of the control circuitry for the system of FIG. 2.

The preferred embodiment of the control circuitry consists of a preprogrammed microprocessor which has sufficient input/output capabilities to interface to optical detectors, said keyboard entry device, said audio alarm, said valve actuating mechanisms, said pressure assist mechanism, said servo position controlled occluding mechanism, and approporiate power supply means. The following circuit description is meant to demonstrate the flow of logic used, but does not schematically represent the actual circuits used. FIG. 4 illustrates a typical block diagram of the control and monitoring circuitry of the system of the present invention. Associated with keyboard 82 on the front panel of the infusion system is a rate pulse generator, which is software generated based on a crystal controlled clock. A predetermined digital value of ml/hr is entered through the keyboard and is scaled through counter 151 to increment and activate rate pulse generator 150 relative to the value entered from the keyboard. This high logical signal passes through logical AND gate 152 along the drive activate line 154 into self-locking OR circuit 156, which puts out a drive signal along drive line 160a,b, and c. Ultimately the drive signal terminates at and activates solenoid control 162 which controls the action of pinch valve stepper motor 100 and may provide activation for a pump assist unit, such as peristaltic pump 36. Not shown on the illustration is a servo controlled line leading to a position sensitive motor which controls the eccentric wheel position (42, FIG. 2) and modulates the degree of inlet tube 12 occlusion. The drive activate signal is directed to stay high for a predetermined amount of time, nominally 100 milliseconds. The higher the setting of flow rate on the keyboard 82, the more rapid the pulses; and the lower the setting on keyboard 82, the longer the time between pulses. The relation between the pulse period and the digital setting is linear. The drive signal out of self-locking OR circuit 156 remains high along line 160a,b, and c through AND gate 164 to energize solenoid control 162 for a predetermined or until stopped by a detector signal.

Each time rate pulse generator 150 sends a signal along drive activate line 154, a pulse is also directed along line 168 (by counter 151) to reset counting clock 170 to zero. Clock 170 then resumes incrementing itself as a part of counter function. It counts until optical detector 64 or 66 and related circuitry, generally designated 172, sends a signal along line 174 for it to stop counting. The clock counts to a certain value, for example, from 0 to 2,000, to accumulate a digital signal to be sent to an analog converter within the clock circuitry. The analog signal goes to timing output 176 along line 178. Timing output 176 has a voltage, thereby, proportional to the amount of time accumulated between the initiation of clock reset zero to the completion of the cycle indicated from optical detector cicuitry 172. This analog signal thus indicates how long each cycle has taken. When clock counter 170 is reset by active line 168, counter 151 is also incremented and contains the number of cycles completed by the system up to that point in time. This value in counter 151 is scaled by factors available within the counter such that the output appears on volume infused indicator 86 in total milliliters. A reset control 182 (FIG. 2) on infusion system 10 inputs into counter 151 through line 184 to reset the system to zero whenever necessary. The drive signal 160 to drive control 162 remains active until one of the detectors 64 or 66 detect control member 58 at an end of volume chamber 56 whereby the control drive signal 160a,b,c is deactivated through line 186 to self-locking OR circuit 156. The deactivation of the signal allows drive control solenoid 162 to rotate stepper motor 100 to its neutral position thereby closing all the valves. The motor not be activated until a new rate pulse is sent. No fluid will flow through the system until the rate pulse is generated opening the valves and starting a new infusion cycle.

The direction of drive control movement, solenoid 162, is further determined by the detector circuitry 172 as it detects the signals from the left detector 64 or the right detector 66. Upon the new rate pulse, the drive signal will be gated through the drive control solenoid in the same manner and direction which the appropriate detector had directed the drive control means to close the valves.

An important facet of this invention is the ability to measure the time taken for control member 58 to travel from one end of tube 56 to the other. This time measurement for the infusion of the discrete and well known volume of tube 56 gives an indication of instantaneous flow through outlet tube 18 during an infusion cycle. By principles of basic physics well-known in the art, the hydrostatic pressure developed by the fluid source is relatively constant. Thus, any short term changes in the flow rates reflect pressure and/or resistance changes at the outlet end 18 of the infusion system. The timing output 176 or its equivalent digital value provides a monitoring source whereby medical personnel can observe clinically significant pressure/resistance changes at the infusion site 20. The time elapsed signal may also be used to initiate alarms for values which are extraordinarily large or may be used in a closed loop feedback servo control with the pressure assist mechanism. The servo position occluding mechanism associated with eccentric wheel 42 (FIG. 2) may be adjusted so that the elapsed time measurement is held to some constant value.

Circuitry to activate an audio-visul alarm is provided to alert personnel to several abnormal occurrences. If the rate pulse genrator issues an activation pulse through line 154 before the drive signal 160 has been deactivated, the high state of 154 is carried by line 200 through gate 202 to gate 206. The output 208 of gate 206 is set high by inputs 160a and 204, activating the self-locking circuit 210 and A-V alarm 212. Circuit 210 maintains the alarm condition until it is manually reset by button 213. This alarm condition prevents a new cycle from starting before the previous cycle has been completed, indicating that the fluid flow is insufficient for that particular keyboard flow rate setting. When each cycle is initiated, line 200 is in the high position, causing circuitry 218 to remain low for a predetermined period of time. Should that particular cycle take longer than this time limit, the output of 218 will go high, passing through 202 to gate 206. If the drive line 106a is still high, then output 208 will activate the alarm. This alarm condition prevents any cycle from taking too long to complete. This alarm signifies low fluid driving pressure (empty fluid source), occlusion of tube 18, or increased patient pressure due to catheter extravasation.

There is further duplication of circuitry for safety reasons. The self-locking OR circuit 156 remains high for a predetermined period of time, for example ten seconds. This assures that even without an alarm condition, the drivve of the motor shall not open the valves for a period greater than ten seconds.

A bubble detector 230, of a type well-known to the art, will be employed along tube 18. Activation of this detector circuitry will directly activate alarm lead 208.

During any alarm state, failsafe measures are taken to prevent any accidental opening of the valves. The activated alarm 212 provides both audio and visual alerts well-known to the art. The high condition of the alarm is inverted by gate 214, causing 216 to lock out any input to gate 164. Thus the output of gate 164, line 160c, is kept de-energized and in the off position. The activated alarm also propogates down line 220 through gate 222, where it is inverted. This low output of gate 222 prevents any inputs from passing through gate 152. Due to the low output of gate 152, drive activate line 154 is held in the low or off mode. The redundant features are designed only for assured patient safety and will not be routinely involved in the operation of the system.

In conjunction with power supply means and interface circuitry well-known in the art, the aforementioned logic scheme can be implemented using a programmable microprocessor, such as the National Semiconductor SC/MP.

MODE OF OPERATION OF THE INVENTION

The invention will be used in the clinical setting as follows:
1. A fluid source is obtained and hung on an IV pole.
2. The disposable, sterile tubing network is unwrapped and connected to the invention, which is hung immediately below the fluid source.
3. The tubing is connected to the fluid source with standard connections familiar to the art.
4. The device is activated at a high flow rate to remove the air from the tubing network, filling the tube with infusate. In practice, this "purging" could be done manually, by moving the pinch valves to the open position.
5. When air is evacuated from the IV line, the system is placed in the standby mode. The fluid filled line is then connected to the patient with the appropriate needle or cannula.
6. The desired flow rate is set by depressing the keyboard entry buttons. This rate will be expressed in terms of ml/hr.
7. An LED display will indicate the flow rate entered by the keyboard selection.
8. A Volume Infused indicator will now be reset to a zero position. As the infusion occurs, this reading will continuously indicate the total amount of fluid received by the patient.
9. The invention is now placed in the infuse mode, whereby the pinch valves begin to open and close in an alternating sequence. The closing of the valves is logically controlled by the optical detectors. The opening of the valves is a function of the flow rate setting. The faster the flow rate, the more frequent the cycles will occur. Each half cycle of the movable will effectively infuse a small (approximately 0.2 ml), discrete, known, reproducible amount of infusate.
10. The pressure which drives the fluid is independent of the flow rate setting on the system. The flow rate of infusate into the patient is a function only of the frequency of cycles which the system goes through. Over a wide range of flow rates (0.5 to 300 ml/hr), infusion can occur at different pressures. The system is capable of intravenous and intra-arterial infusions The use of variable pressure independent of the flow rate setting is a very significant advance from prior art.
11. When gravity pressures are insufficient to move the fluid, i.e., arterial infusions, viscous material infusions, or very rapid infusions; a built-in peristaltic pump assist mechanism may be employed. This pump assist can add to the driving force of the fluid without changing the flow rate. Provisions are made to incrementally affect the tubing such that the degree of assistance obtained from the pump is adjustable by manual or automatic control. This variable pressure pump feature is clearly unique to the art.
12. During most intravenous infusions, the pressure of gravity is sufficient to drive the fluid into the vein. If pressure changes occur at the infusion site, it is a clinically significant event. The invention will monitor the flow of fluid during the "valves open" portion of the cycle. By measuring the time taken for the control member to traverse across the control tube, an indication of flow is obtained. By physical principles, this flow measurement is directly and linearly related to the resistance and/or pressure at the infusion site. This "elapsed time" measurement may be displayed on a type of visual display, i.e. oscilloscopes or strip chart recorders. Changes in pressure and/or resistance will cause characteristic changes in the "elapsed time" values, signalling the need for appropriate clinical attention. The invention is the first device to both control flow accurately and monitor flow patterns. This unique measurement capability could play an important diagnostic role in infusion therapy. The character of the "elapsed time" changes could be analyzed for differential diagnosis of the particular type of abnormality present. The system of the invention provides a mechanism for reliably detecting the clinical conditions of leaking lines, clogging lines, and infiltration.

13. In a high pressure application, where the peristaltic type pump is activated, the degree of external pressure applied to the tubing may be under servo control. A nominal constant value is preprogrammed into the system to represent a certain "elapsed time" measurement. The actual "elapsed time" is computed for each infusion cycle. On cycles which are completed more quickly than the preprogrammed value, no pressure assist is necessary and none is provided. On cycles which are completed more slowly than the preprogrammed value, the servo controlled occlusion of the tube is increased, provided an increase in effective infusate pressure. This increase in pressure assist will continue each cycle until the "elapsed time" of any given cycle reaches the preprogrammed value. Through numerical techniques well-known in the art, the servo feedback subsystem can be modified to provide varying degrees of responsiveness and stability.

Numerous modifications, embodiments, and changes will be readily apparent to those skilled in the art. The invention, therefore is not to be construed to be strictly limited to the foregoing disclosure as such changes, modifications, and embodiments may be made without departing from the spirit and scope of the present invention.

I claim:

1. An intravenous infusion system capable of regulating flow from an infusate fluid supply means through a disposable tubing supply network into animate bodies, most notably medical patients, comprising:
   a reciprocal metering means allowing discrete, known quantities of said fluid to move at specific intervals through said disposable tubing supply network;
   circuit means for regulating the frequency and number of said discrete fluid quantities passed into the patient;
   means for selectively externally increasing the available driving pressure of said infusate;
   means for monitoring fluid velocity during moments of infusion through said tubing means;
   means for computing and displaying clinical status conditions based on said fluid velocity;
   wherein said reciprocal metering means comprise:
   a fluid volume control apparatus capable of receiving an inlet tube from an infusion supply means and an outlet tube connected to a cannula for infusion of fluids into animate bodies comprising:
   a ported, divaricated delivery tube which receives and diverges into portions from said inlet tube and converges and receives said outlet tube;
   a transverse volume control tube, ported at its ends, intermediately disposed between said diverging portions of said divaricated delivery tube, said diverging portions being ported therewith with said control tube having internal dimensions such that each infusion cycle will deliver less than 1.0 ml of infusate;
   means associated with said diverging portions of said delivery tube for restricting and regulating fluid flow through said delivery tube being positioned such that said volume control tube port connections are interposed therebetween;
   means for alternately operating said infusion flow regulation and restriction means in a diagonally paired tandem fashion;
   a control member movably positioned in a substantially fluid tight relation within said control tube, and optical detection means positioned about each end of said control tube at the connection of said delivery tube portions for detection of said control member;
   and wherein said means for monitoring fluid velocity during moments of infusion comprise:
   electrical output means from said optical detectors which are measured by the controlling circuitry in relation to the initiation of each infusion cycle to determine the time taken for said control member to leave the presence of one said detector means and travel through said volume control tube into the presence of said detection means at the other end of said control tube;
   and wherein said means for externally increasing the available driving pressure of said infusate fluid comprises:
   a motor-driven eccentric means and an associated occluding means, such as a roller or peristaltic pump, for squeezing said inlet tube in a well-known time-space relationship, causing fluid to be propagated in a single direction through said tubing network;
   an electromechanical switch to selectively activate and deactivate said motor-driven eccentric means and said associated occluding means;
   and wherein said circuit means for regulating the frequency and number of said discrete fluid quantities delivered to the patient consists of a programmed microprocessor and associated interface and input/output circuit means;
   and wherein said means for computing clinical status conditions provides distinct indications for infusion rate, volume infused, and abnormally slow flow through said volume tube.

2. The apparatus as recited in or claim 1 wherein said means for externally increasing the available driving pressure of said infusate fluid is modulated with a servo feedback mechanism based on said fluid velocities and said occluding means, to provide variable degrees of pressure assist.

3. The apparatus as recited in claim 2 wherein the servo mechanism consists of a position controlled motor mechanically linked to said occluding means and controlled by said microprocessor circuit means, wherein said motor position is determined by a mathematical function of said fluid velocity and a preprogrammed constant value in the system, said function providing a stable feedback mechanism to minimize the level of infusion pressure necessary for a given infusion rate.

4. The apparatus as recited in claim 3 further including a rechargeable battery power source for all circuitry, motors, indicators; a digital keyboard data entry device; and display indications for flow rate, volume infused, total volume to be infused, purge state, low battery charge, incorrect keyboard entry, volume limit alarm, slow flow alarm, pump assist indication, and for electronic self-test displays.

* * * * *